(12) United States Patent
Chaves, Sr. et al.

(10) Patent No.: US 11,135,359 B2
(45) Date of Patent: Oct. 5, 2021

(54) INFUSION DEVICE WITH STABILIZER MEMBER

(71) Applicant: Becton, Dickinson and Company, Franklin Lakes, NJ (US)

(72) Inventors: Alex Sousa Chaves, Sr., Auburn, MA (US); Victor Isaac Politis, Framingham, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 57 days.

(21) Appl. No.: 16/320,656

(22) PCT Filed: Jul. 20, 2017

(86) PCT No.: PCT/US2017/043145
§ 371 (c)(1),
(2) Date: Jan. 25, 2019

(87) PCT Pub. No.: WO2018/022433
PCT Pub. Date: Feb. 1, 2018

(65) Prior Publication Data
US 2019/0160226 A1    May 30, 2019

Related U.S. Application Data

(60) Provisional application No. 62/367,344, filed on Jul. 27, 2016.

(51) Int. Cl.
*A61M 5/158* (2006.01)
*A61M 5/32* (2006.01)
*A61M 5/142* (2006.01)

(52) U.S. Cl.
CPC ............ *A61M 5/158* (2013.01); *A61M 5/142* (2013.01); *A61M 5/3202* (2013.01); *A61M 2005/1585* (2013.01); *A61M 2005/1586* (2013.01)

(58) Field of Classification Search
CPC .... A61M 5/158; A61M 5/142; A61M 5/3202; A61M 2005/1585; A61M 2005/1586
See application file for complete search history.

(56) References Cited

U.S. PATENT DOCUMENTS

2007/0191771 A1    8/2007 Moyer
2007/0191772 A1    8/2007 Wojcik
(Continued)

OTHER PUBLICATIONS

International Search Report dated Oct. 10, 2017, which issued in the corresponding PCT Patent Application No. PCT/US2017/043145.

*Primary Examiner* — Lauren P Farrar
(74) *Attorney, Agent, or Firm* — Dickinson Wright PLLC (57) ABSTRACT

An infusion device system includes a base (12) for removably coupling to a delivery device, a needle hub (22) supporting an insertion needle (20) and a catheter (18) for delivering a substance to a patient. The infusion device includes a needle shield (24) for covering the insertion needle (20) after inserting the catheter (18) into the patient. The needle hub (22) includes a least one leg (70) extending from the needle shield (24) to stabilize the needle shield (24) and needle hub (12) relative to the base. In one embodiment, the legs (70) can include a latching tab (74) to couple to the needle hub (22) to resist separation of the needle hub from the base (12) until the legs are deflected outward to release the needle hub (22).

17 Claims, 12 Drawing Sheets

(56) References Cited

U.S. PATENT DOCUMENTS

| | | |
|---|---|---|
| 2012/0065587 A1 | 3/2012 | Barron et al. |
| 2012/0123344 A1* | 5/2012 | Hornig .................. A61M 5/158 |
| | | 604/180 |
| 2014/0088509 A1 | 3/2014 | Sonderegger et al. |
| 2014/0039458 A1 | 6/2014 | Cole et al. |
| 2014/0316379 A1* | 10/2014 | Sonderegger ......... A61M 5/142 |
| | | 604/506 |
| 2014/0350485 A1 | 11/2014 | Sonderegger et al. |

* cited by examiner

INFUSION DEVICE WITH STABILIZER MEMBER

This application claims priority under 35 U.S.C. § 119(e) from U.S. Provisional Application Ser. No. 62/367,344, filed on Jul. 27, 2016, which is incorporated herein by reference in its entirety.

FIELD OF THE INVENTION

The present invention relates generally to infusion devices, and more particularly, to subcutaneous infusion devices to be used in conjunction with an infusion pump in the infusion of insulin and other medicaments. The infusion device includes a needle hub assembly having a stabilizing member to stabilize the hub assembly relative to base of the infusion device.

BACKGROUND OF THE INVENTION

One mode of insulin infusion treatment includes infusion pump therapy via a catheter, needle or other type of cannula. Infusion pumps offer the advantages of continuous infusion of insulin, precision dosing, and programmable delivery schedules. Together, these advantages result in more accurate blood glucose control. In this mode of insulin infusion treatment, the infusion pump remains attached to the user and required doses of insulin are delivered to the user via the pump.

One type of cannula is a catheter, which generally is a tube that can be inserted into the body to permit the administration of fluids. In infusion pump therapy, the types and sizes of the catheter may vary, but generally, the catheter is a thin, flexible tube. In some uses, however, it may be larger and/or rigid. A rigid, hollow, metal needle may also be used in place of a soft plastic catheter.

One type of conventional infusion device, known as an infusion set, includes a catheter assembly connected to a pump via a tubing set, and a separate insertion device inserts and/or attaches the catheter assembly into/to a user via an introducer needle provided as part of the infusion set. The infusion set and insertion device can also be combined into one unit.

Another type of insulin infusion device, known as a "patch pump," has recently become available. Unlike a conventional infusion pump, a patch pump is an integrated device that combines most or all of the fluid components in a single housing that is adhesively attached to an infusion site, and does not require the use of a separate tubing set. A patch pump adheres to the skin, contains insulin (or other medication), and delivers the drug over a period of time, either transdermal, or via an integrated subcutaneous mini-catheter. Some patch pumps communicate with a separate controller device wirelessly (such as one sold under the brand name OmniPod®), while others are completely self-contained.

A conventional infusion device can include a fluid connector, which may be releasably attached to a base that can be secured to a user's skin. An infusion pump supplies fluid to a catheter via the fluid connector/base engagement.

With such devices, however, there are concerns over the difficulty of balancing the force required to disconnect the tubing without pulling the catheter from the user's skin versus having enough retention force to secure the infusion components for everyday infusion. Another concern is that there may be a need to design a rotational lock between the fluid connector and the base. Yet another concern is that the separation force needs to be designed such that if a user accidentally snags the extension tubing on an external structure (e.g., a doorknob), the extension tubing will disconnect from the fluid connector without removing the catheter from the user's skin, thus saving the patient from the need to obtain, connect and re-insert a new infusion device.

Additionally, to protect the cannula and/or introducer needle prior to insertion, conventional devices often include a needle guard that is removed prior to use. These needle guards, however, are often very small and may be difficult to grasp, particularly for people with impaired dexterity. Additionally, conventional needle guards are often held in place by friction alone. To remove such needle guards, patients must pull and/or twist the needle guard, and the axial force required to remove such needle guards may vary widely, for example, based on manufacturing tolerances. Further, with such needle guards, once the coefficient of static friction is overcome, the guard may separate quickly, without providing an opportunity for a user to modify the applied force and potentially resulting in a needle-stick injury. Further, there is a risk that the needle guard can contact the needle during removal, potentially dulling the cannula or introducer needle.

SUMMARY OF THE INVENTION

An object of embodiments of the present invention is to substantially address the above and other concerns, and provide improved infusion devices. Another object of embodiments of the present invention is to provide an infusion device having a needle hub assembly with a stabilizing member.

These and other objects are substantially achieved by providing an infusion device, including a base having a distal side for attaching to a patient at an infusion site, a fluid connector that can be removably coupled to the base, and a needle hub assembly. The needle hub assembly includes a needle hub having a moveable needle shield for covering an insertion needle after removing from the base. The base includes a base section extending proximally from a surface of the base, with a coupling for connecting to the fluid connector. The needle hub supports an insertion needle that extends through a catheter coupled to the base for the insertion of the catheter into the patient. A needle shield slides within the needle hub during the separation of the needle hub from the base to cover the insertion needle to prevent injury to the patient.

The needle hub assembly of the invention includes a connection end for connecting to the base of the infusion device for insertion of the insertion needle and catheter into the patient. The needle hub assembly has a needle shield for sliding to an extended position after insertion to slide over the insertion needle. The needle hub slides over the needle shield by pulling upward on the needle hub to retract the insertion needle into the needle shield. The needle hub in the operating position engages the needle shield to prevent the needle shield from separating from the base. Sliding the needle hub to a position where the needle shield is in an extended position enables the needle shield to separate from the base.

The needle shield in one embodiment of the invention includes at least one and generally two stabilizing members. The stabilizing member in one embodiment includes legs that extend outwardly to engage the bottom end of the needle hub and the base. The legs can have detents, hooks or latches that can couple to the needle hub to inhibit separation or sliding movement of the needle hub relative the needle shield. The legs can be disengaged from the needle hub whereby the needle hub can slide upward with respect the needle shield. In one embodiment, the legs are flexible and can be pushed downward or away from the needle hub to release the needle hub and enable the needle hub to slide upward to allow separation of the needle shield from the base.

These and other objects are also substantially achieved by providing an infusion device comprising a base, a needle hub and a needle shield. The base includes a catheter and a coupling for connecting to a delivery device for supplying a drug or medication to the patient. The needle hub has an insertion needle fixed to the needle hub that extends from the needle hub and through the catheter. The needle hub has a bottom end for contacting the base. The needle shield is received in the needle hub and is slideable with respect to the needle hub from a first retracted position to a second extended position to cover the insertion needle. The needle shield has a bottom end removably coupled to the coupling of the base and has at least one outwardly extending leg that extends radially from the needle shield a distance from the needle hub to stabilized the needle hub relative to the base.

The features of the invention are further attained by providing an infusion device comprising a base, a needle hub and a needle shield. The base includes a catheter and a coupling for connecting to a delivery device for supplying a drug or medication to the patient. The needle hub has an insertion needle fixed to the needle hub that extends from the hub and through the catheter. The needle hub has a bottom end for contacting the base. The needle shield is received in the needle hub for sliding with respect to the needle hub from a first retracted position to a second extended position to cover the insertion needle. The needle shield has a bottom end removably coupled to the coupling of the base. At least one leg extends outwardly from the bottom end of the needle shield and is coupled to the needle hub to resist movement relative to the needle hub. The leg can be released or unlatched from the needle hub to enable the needle hub to slide upward relative to the needle shield and allow separation of the needle shield from the base.

The advantages of the invention are further attained by providing a needle hub assembly for an infusion device comprising a needle hub and a needle shield. The needle hub has a insertion needle with a proximal end coupled to the needle hub and a distal end adapter for extending through a catheter of the infusion device. The needle hub has an open bottom end configured for contacting a base of the infusion device. The needle shield is received in the needle hub for sliding with respect to the needle hub between a first retracted position within the needle hub and a second extended position extending from the open bottom end of the needle hub. At least one leg extends radially outward from the needle shield and contacts the bottom edge of the needle hub. The at least one leg has a length to contact the base of the infusion device to stabilize the needle shield relative to the base of the infusion device.

Additional and/or other aspects and advantages of the present invention will be set forth in the description that follows, or will be apparent from the description, or may be learned by practice of the invention.

BRIEF DESCRIPTION OF THE DRAWINGS

The various objects, advantages and novel features of the exemplary embodiments of the present invention will be more readily appreciated from the following detailed description when read in conjunction with the accompanying drawings, in which.

DETAILED DESCRIPTION OF EXEMPLARY EMBODIMENTS

Reference will now be made in detail to embodiments of the present invention, which are illustrated in the accompanying drawings, wherein like reference numerals refer to like elements throughout. The embodiments described herein exemplify, but do not limit, the present invention by referring to the drawings. As will be understood by one skilled in the art, terms such as up, down, bottom, top, proximal, and distal are relative, and are employed to aid illustration, but are not limiting.

Figure 1:
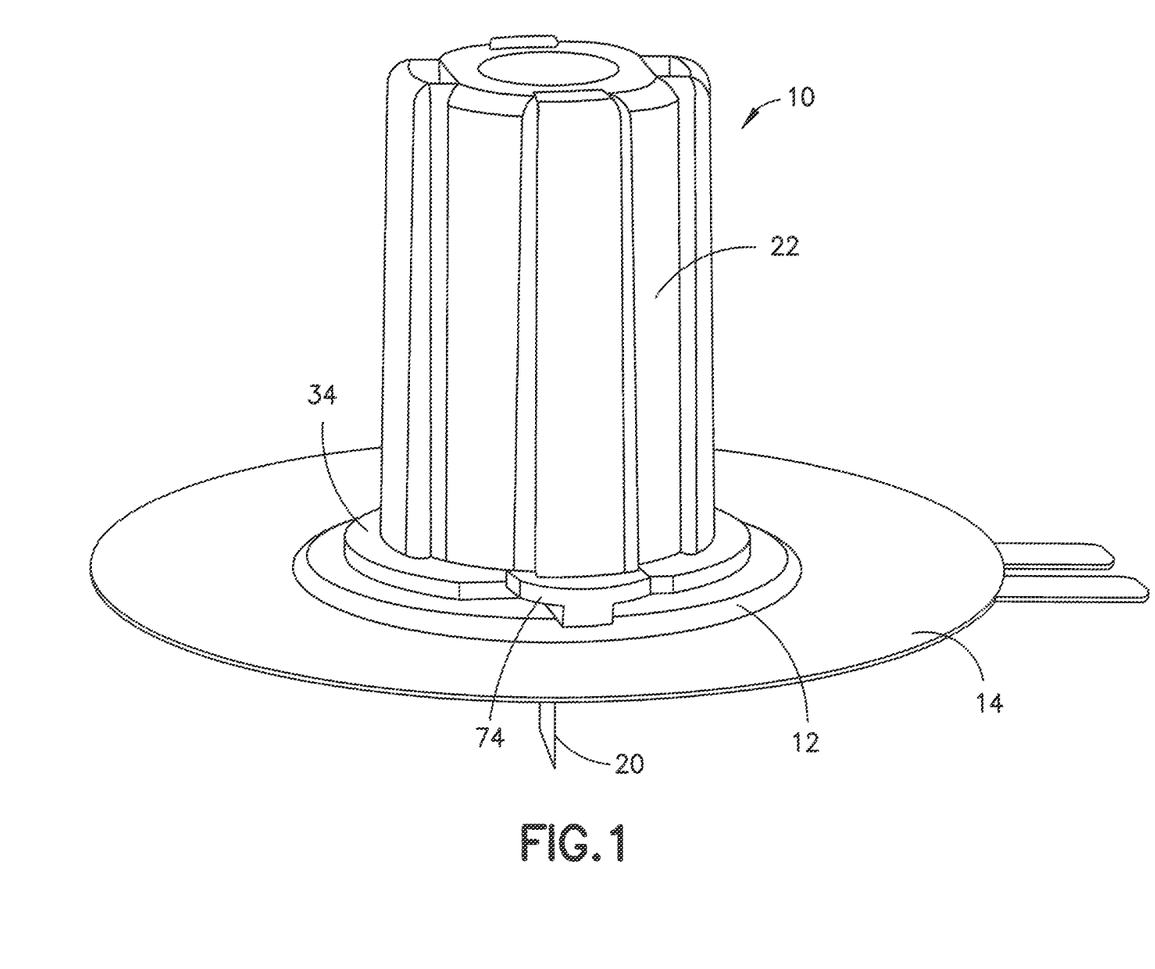
FIG. 1 is a perspective view of a needle hub assembly connected to an infusion device base in accordance with an exemplary embodiment of the present invention.

FIG. 1 illustrates an exemplary embodiment of an infusion device, in this case an infusion set, comprising an introducer needle hub assembly 10 engaged with a base 12. The base 12 engages a flexible disc 14 positioned between the base 12 and a user. The flexible disc 14 provides improved comfort and mobility of the device because it moves with the user during physical activity while minimizing contact of the rigid portions of the base 12 with the user. The flexible disc 14 is attached to an adhesive patch or pad 16 having an adhesive backing, which is used to secure the base 12 to the user's skin. FIG. 1 illustrates a state in which the introducer needle hub assembly 10 and base 12 are ready for insertion of a soft (flexible) catheter 18 and an introducer needle 20 into the user.

Figure 2:
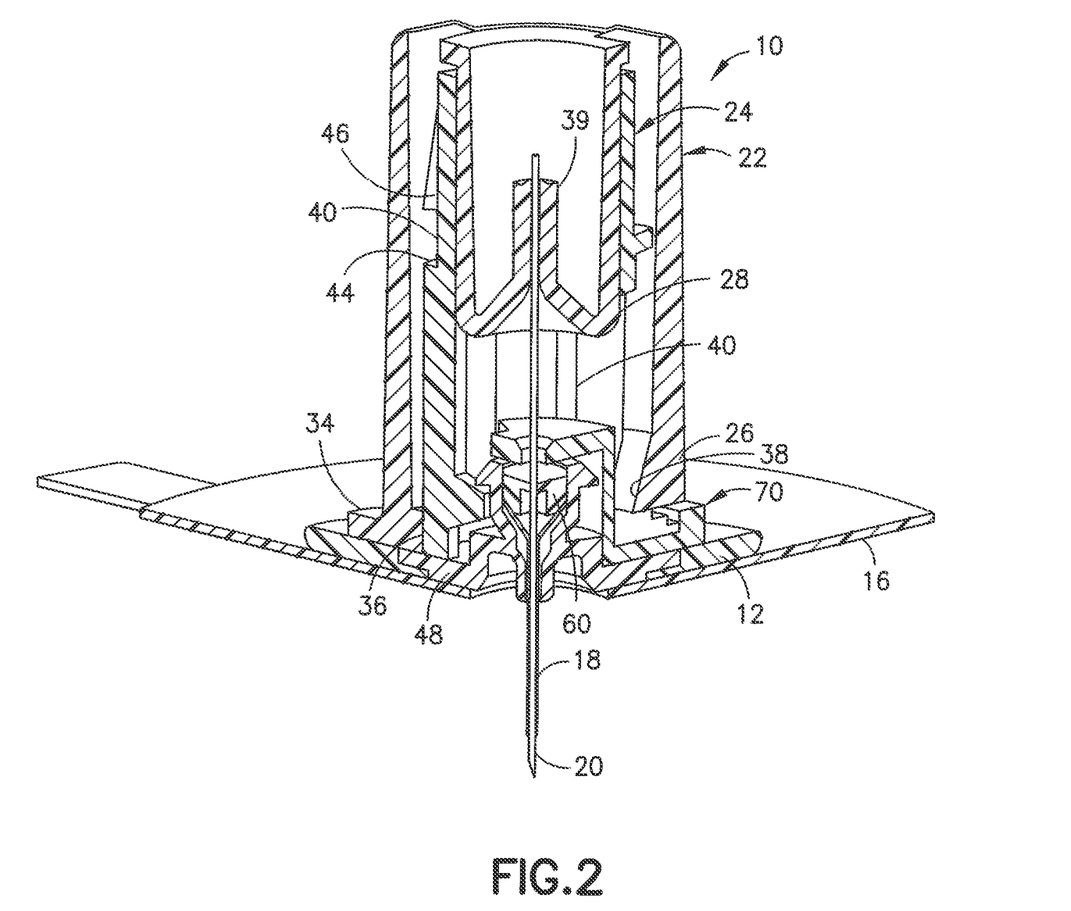
FIG. 2 is a cross-sectional view of the needle hub assembly and base of FIG. 1.
Figure 3:
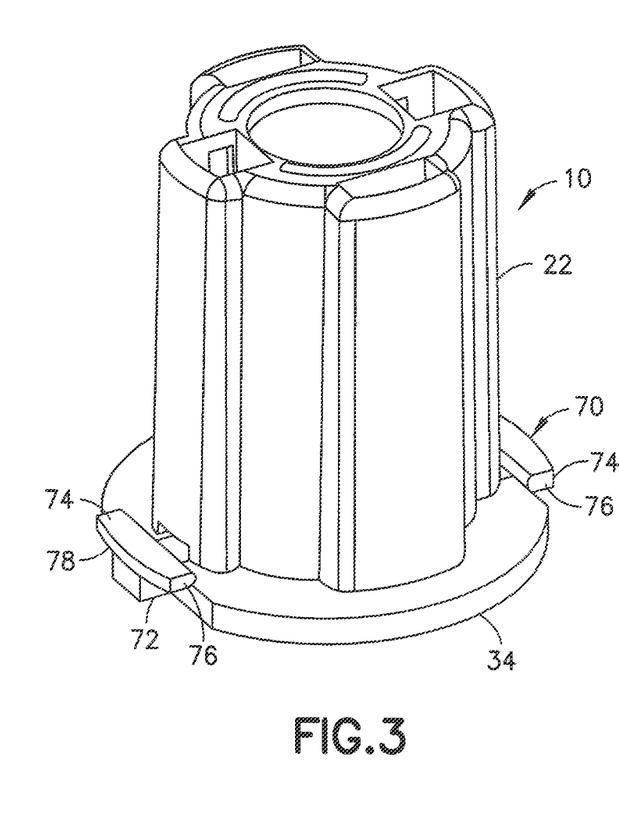
FIG. 3 is a perspective view of the needle hub and needle shield of FIG. 1.
Figure 4:
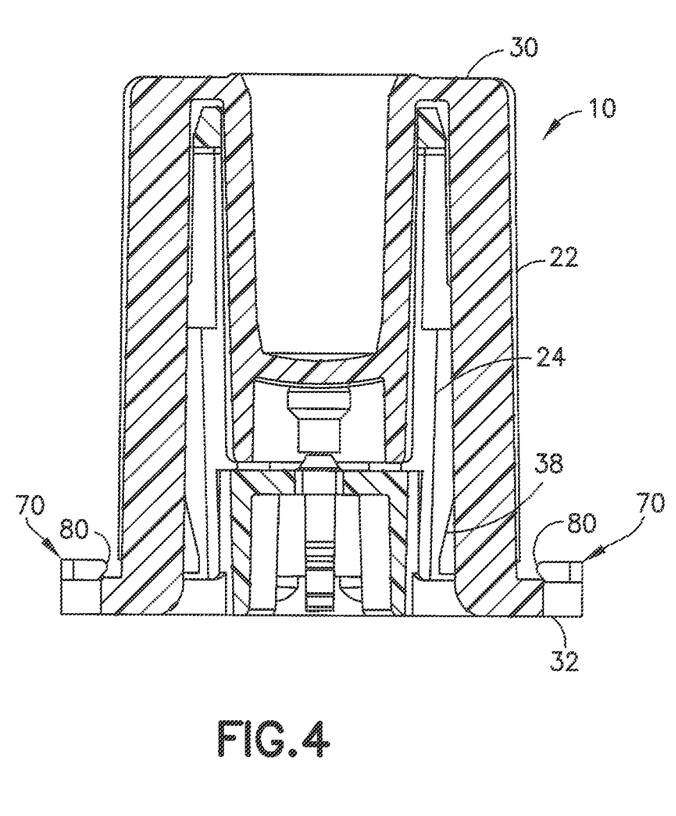
FIG. 4 is a cross-sectional view of the needle hub assembly of FIG. 3.

FIG. 2 is a cross-sectional view of the base 12 and introducer needle hub assembly 10 shown in FIG. 1. The needle hub assembly 10 includes a needle hub 22 and a needle shield 24. Needle hub 20 includes a substantially cylindrical outer sleeve 26 and an inner sleeve 28 spaced apart a distance to receive the needle shield 24. The outer sleeve 26 has a top end 30 and a bottom end 32 with an outwardly extending flange 34 for contacting the base 12 when the needle hub assembly 10 is coupled to the base 12. The bottom end 32 has an inner surface with a detent 36 extending inwardly in a radial direction relative to the outer sleeve as shown in FIGS. 2 and 3. Spaced a slight distance from the bottom end 32 is a locking tab 38 for latching the position of the needle hub 22 relative to the needle shield 24.

The introducer needle 20 is fixed to a needle mounting structure 40 of the inner sleeve 28 within the needle hub 22 to fix the introducer needle 20 against axial movement relative to the needle hub 22. The needle hub 22 is used to insert the introducer needle 20 and the catheter 18 into the patient without requiring the user to hold or manipulate the introducer needle 20 directly. The introducer needle 20 can be a hollow or solid stainless steel needle with a sharp beveled distal end. As shown, the introducer needle 20 has a length to extend from the distal end of the catheter 18 a distance to enable penetration into the skin to insert the catheter to a desired depth.

Figure 9:
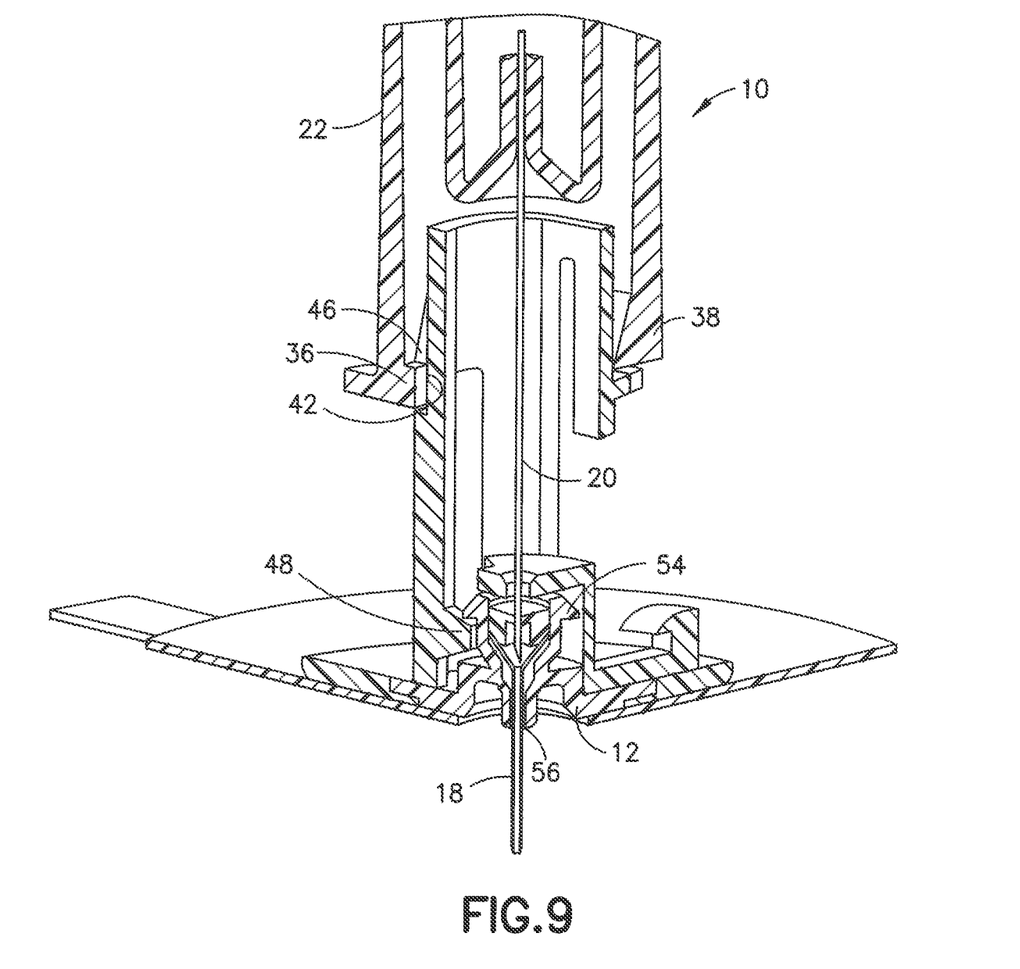
FIG. 9 is a cross-sectional view showing the needle shield in the extended position.

The needle shield 24 has a shape to slide between the outer sleeve 26 and inner sleeve 28 between a first retracted position shown in FIG. 2 and an extended position shown in FIG. 9 where the inserter needle 20 is retracted within the needle shield 24. The needle shield 24 includes an inwardly extending latching member or latching beam 48 for engaging the coupling member 49 of the base 12 to retain the needle shield on the base during insertion of the needle 20 and catheter into the patient. In the embodiment shown, the needle shield 24 includes a longitudinal slit 40 to enable the wall of the needle shield to bend outwardly for coupling and separating the needle shield from the coupling 49 of the base 12. Toward the upper end of the needle shield is a recess 42 formed by a ledge 44 and detent 46 to receive the inwardly extending detent 36 of the needle hub 22 when the needle hub slides upwardly with respect to the needle shield 24.

The inwardly extending detent 36 in the original position engages the outer surface of the needle shield as shown in FIG. 2 to retain the latching beam 48 of the needle shield 24 in engagement with the coupling of the base 12. The needle hub 22 is manually pulled upwardly to slide along the needle shield to the position shown in FIG. 9. The needle shield 24 can then flex outwardly to release from the coupling 49 of the base 12. The needle shield is locked in the extended position by the detent 36 received in the recess 42 formed in the outer surface of the needle shield 24 so that the needle shield 24 is retained in the extended position to cover the insertion needle 20 when the hub assembly 10 is separated from the base 12.

Figure 10:
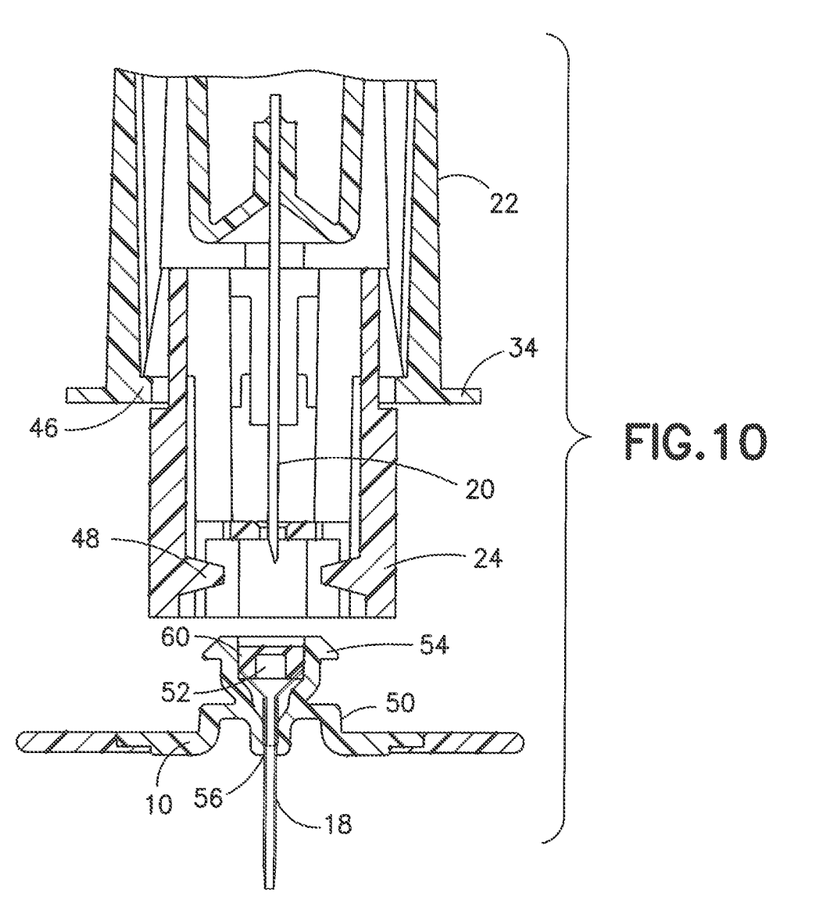
FIG. 10 is a cross-sectional view showing the needle hub and needle shield separated from the base of the infusion device.

As shown in FIG. 10 the base 12 includes post 50 surrounding an internal cavity 52. The mushroom-shaped coupling 54 is disposed at the proximal end of the post 50. An internal passage 56 generally extends through the center of the base 12 providing a fluid passageway through the base 12. As shown in FIG. 9, the internal cavity 52 of the base 12 receives a retaining wedge and the passage 56 receives the catheter 18. The wedge has a funnel shape with a hollow center portion that narrows from a broad end to a narrow end. The narrow end of the wedge has a tapered end used to receive a terminal end of the catheter 18. The catheter 18 is forced over the narrow end of the wedge and the wedge/catheter assembly is inserted into the internal cavity 52 of the base 12.

Due to the flexible characteristics of the catheter 18, it may have a tendency to bunch up within the base 12 and therefore, the cavity area 52 has a sufficient size to accommodate excess catheter 18 material that may accumulate within the base 12 during the installation of the catheter onto the wedge.

A pre-slit resilient septum 60 is also retained within the internal cavity 52 of the base 12 as shown in FIG. 2. According to an exemplary embodiment, the septum 60 is held in place within the base 12 by a press fit, which provides a friction fit between the septum 60 and both the base 12 and the wedge. Alternatively, the septum 60 may be fixed within the base 12 by an adhesive or by swaging plastic material from the base 12 over the top of the septum, or a combination of the above-described methods.

The base 12 can be made from first and second molded shots. The second molded shot may be of the same material as the first shot or may be of a different, more flexible material, which may include a silicone or thermoplastic elastomer, and thus, may be the flexible disc. Cut outs or holes in the base 12 become filled with the material for the flexible disc, and thus, facilitate bonding between the base 12 and the flexible disc.

A fluid connector can be connected to the coupling of the base 12 during use to deliver the drug or medication to the patient. One example of a fluid connector and septum are disclosed in WO 2013/086463 which is incorporated by reference in its entirety.

The self-sealing resilient septum 60 can have a pre-pierced center to receive the blunt molded cannula from the fluid connector and facilitate penetration of the septum 60. According to one embodiment, the septum 60 is under inward radial compression to ensure a seal at all times, with or without the molded cannula being present. The septum 60 can be made of a soft resilient material including, but not limited to silicones, isoprene rubbers, or bromobutyl rubbers. The septum 60 can be made from a combination of these materials as well. The septum 60 ensures a complete seal during infusion and when the fluid connector is disconnected from the base 12. The slit geometry of the septum 60 may be a single straight slit or multiple, intersecting straight slits. The slit may also be curved to ensure a complete seal during infusion and while the connector hub is disconnected from the base 12.

Figure 5:
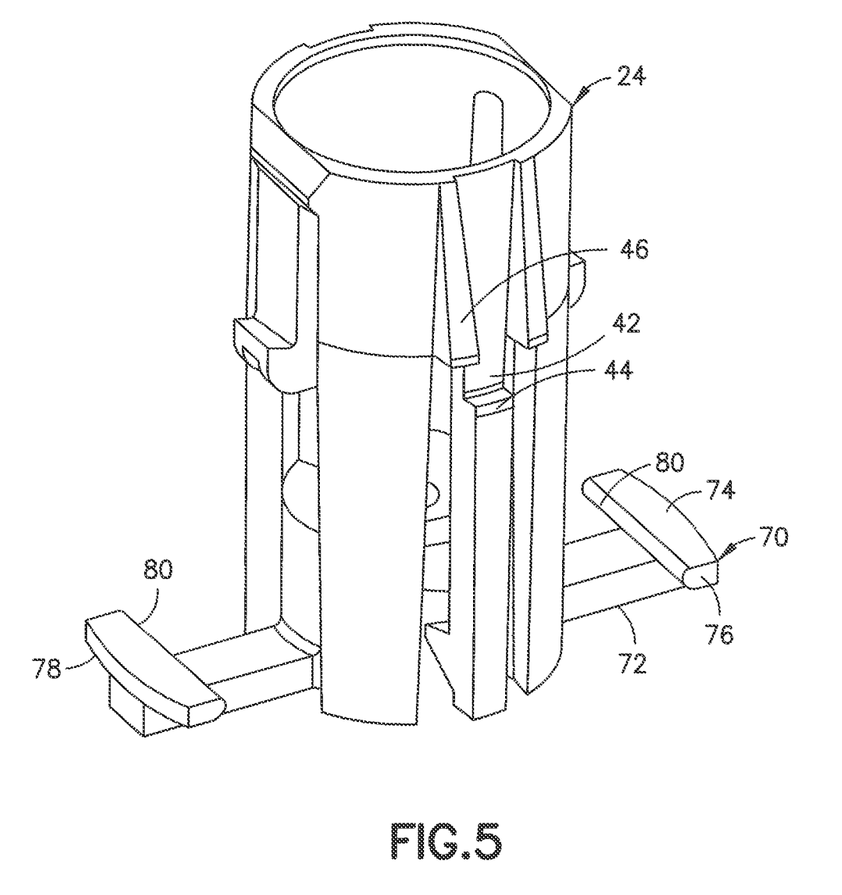
FIG. 5 is a perspective view of the needle shield of FIG. 1 in accordance with an embodiment of the present invention.
Figure 6:
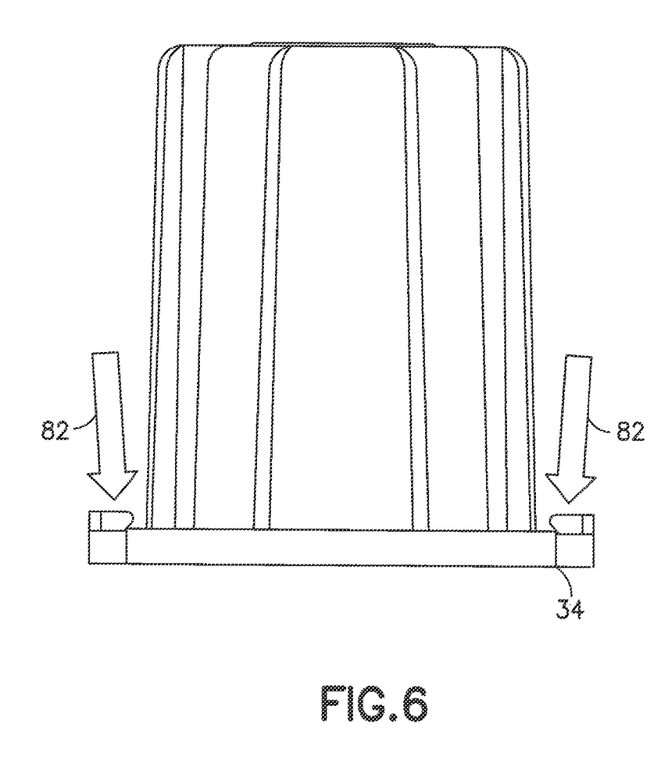
FIG. 6 is a side view of the needle hub and needle shield of FIG. 1 showing the needle hub in the original position.
Figure 7:
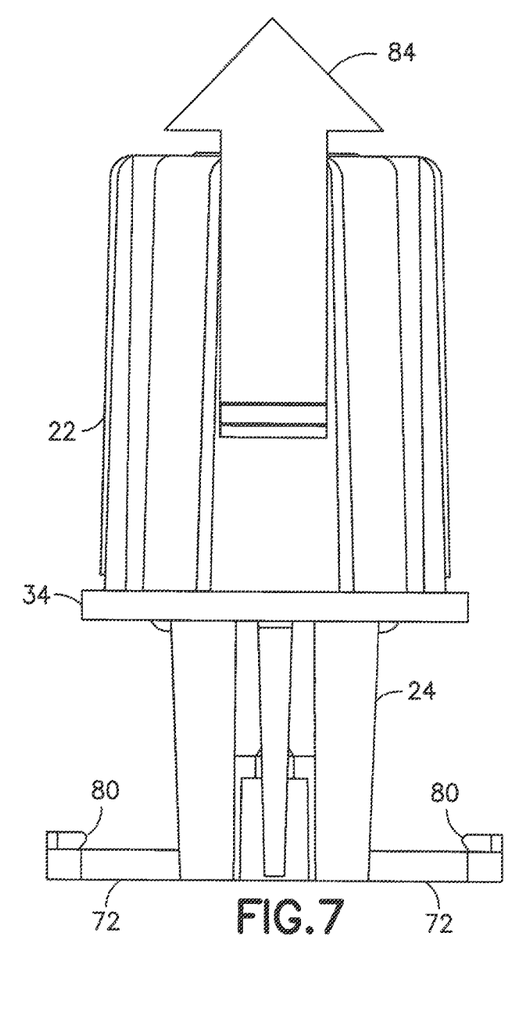
FIG. 7 is a side view showing the needle hub sliding relative to the needle shield.

Referring to FIGS. 5-7, the needle shield 24 has a latch member formed from a leg 70 that extends outwardly from the bottom end of the needle shield 24 for latching or coupling with the needle hub 22. The needle shield 24 has at least one leg and typically more than one leg. In the embodiment shown, two legs extend from the bottom end of the needle shield in opposite directions and are diametrically opposed for coupling with opposite side edges of the needle hub 22. The legs 70 form the latching member for connecting with the flange of the needle hub 22 to retain the needle hub 22 coupled to the needle shield 24.

In one embodiment of the invention, the legs 70 extend outwardly a distance to stabilize the needle hub 22 and the needle shield 24 during use and resist tilting, bending or deflection of the needle hub assembly 10 relative to the base 10. The legs 70 have a length to extend radially outward a distance greater than the outer dimension of the needle hub 22 and have a bottom surface to contact the base 10 when the needle hub assembly is coupled to the base 10.

The legs 70 have a length to maintain the needle hub assembly 10 in a upright, substantially perpendicular position relative the base 10 and stabilize the needle hub assembly 10. The legs hold the needle shield 24 in an upright position with respect to the axis of the coupling on the base 12 during the sliding movement of the needle hub 22 while the needle shield 24 is still attached to the coupling of the base 10. A tilting movement of the needle shield 24 while the needle hub is being pulled upward from the base 10 can cause separation of the needle shield 24 from the coupling before the insertion needle 20 is fully retracted within the needle shield. The legs can reduce the twisting or bending of the needle shield during the sliding movement of the needle hub on the needle shield.

The legs 70 include a beam 72 that extends in a radial direction with respect to the needle shield 24. The legs 70 are preferably sufficiently flexible to be able to deflect when sufficient pressure is applied to release the needle hub 22 from the needle shield 24. The distal end of each leg 70 includes a latching tab 74 extending upwardly from the top surface of the leg 70. As shown in FIG. 5, each latching tab 74 has two outwardly extending portions defining flat end surfaces 76, a rounded outer edge 78, and an inner latching edge 80. The latching edge 80 is defined by a rounded surface with a slight undercut to form the latching edge 80. As shown in FIG. 6, inner latching edge 80 hooks over the flange 34 of the needle hub 22 to retain the needle hub 22 connected to the needle shield and prevent separation until the latching edge 80 is released from the flange 34.

The inner latching edge 80 in the embodiment shown has a slight curved surface with an inclined bottom face to slide over the flange 34 when the needle hub is released from the needle shield 24 and an inclined upper surface. In other embodiments, the latching edge can be a blunt edge or have a hook-like shape that is able to engage the flange of the needle hub and be released from the flange of the needle hub.

In the embodiment illustrated, the latching tabs 74 are formed on the upper surface of the beams 72 to engage the flange of the needle hub. In other embodiments, the latching tabs can be formed with the distal end of the beams and have a vertical dimension or height extending from the bottom surface of the beams to a location for coupling with the flange of the needle hub. The latching tabs can have a dimension and can be oriented to contact the base 10 to resist lateral tilting by the needle shield when coupled to the base.

A downward manual pressure in the direction of arrows 82 applied to the latching tabs 74 flexes the legs 70 away from the flange 34 to release the flange 34 from the latching tab 74. The needle hub 22 can then be pulled upward in the direction of arrow 84 shown in FIG. 7 to slide the needle hub 22 upwardly with respect to the needle shield 24 to the position where the needle shield 24 is in the extended position to cover the insertion needle 20. For clarity the insertion needle is not shown in FIGS. 6 and 7.

FIGS. 2 and 8-10 illustrate the sequence of steps that occur after the user has inserted the catheter 18. These figures illustrate the operation of removing the needle hub assembly 10 from the base 12. During use, the user presses downwardly on the latching tabs 74 and pulls on the outer needle hub 22 in the direction away from the base 12 to remove and retract the introducer needle 20 from catheter 18. According to one embodiment, the outer needle hub 22 and inner needle shield 24 are both made of rigid plastic materials that have some degree of flexibility.

In more detail, FIG. 2 is a quarter-sectional view illustrating an initial state of the needle hub assembly 10 and a first position of the outer needle hub 22 relative to the inner needle shield 24, in which the detent 36 of the needle hub 22 contacts the base 12 and also contacts the outer surface of the needle shield 24 opposite the detent forming a cantilevered latch beam 48 of the needle shield 24 to maintain engagement of the latching beam 48 with the base 12 beneath the mushroom-shaped coupling 54. According to one embodiment, the detent 36 biases the latch beam 48 radially inward toward coupling 54.

Figure 8:
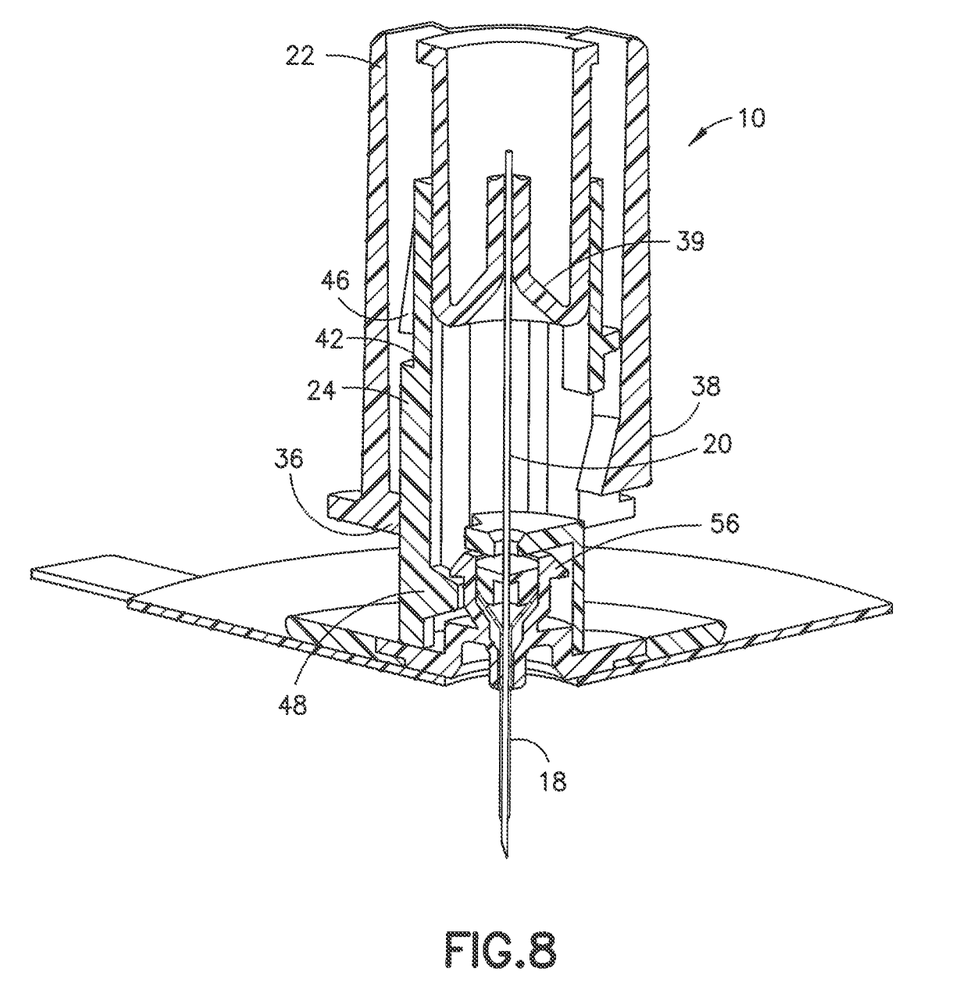
FIG. 8 is a cross-sectional view showing the needle hub sliding relative to the needle shield to retract the insertion needle from the catheter.

FIG. 8 illustrates the orientation of the needle hub assembly 10 while the user is axially displacing the outer needle hub 22, but before it has completed its stroke relative to the inner needle shield 24. In this state, the needle hub 22 and detent 36 prevent latch beam 48 from disengaging from the base 12. The detent 36 holds the latch beam in place against the base 12. According to one embodiment, the needle shield 24 is locked onto the base 12 while the outer needle hub 22 is being axially displaced relative to the needle shield 24.

FIG. 9 illustrates the completely displaced position of the needle hub 22 with respect to the needle shield 24. In this state, the detent 36 no longer prevents the latch beam 48 from disengaging from the base 12. The detent 36 is instead disposed in the recess 42 on the needle shield 24 and engaged with the detent 36 formed on the needle shield 24. The detent 46 engages a top side of the detent 46, thereby preventing further proximal displacement of the needle hub 22 relative to the needle shield 24. The detent 36 received in the recess 42 prevents the needle shield 24 from retracting into the needle hub 24. Additionally, because the detent 36 is no longer pressing on the latch beam 48, the latch beam 48 can disengage from the base 12. The locking tab 38 rides over an inner shield latch and the bottom of the detent to prevent distal displacement of the needle hub 22 relative to the needle shield 24.

The latch beam 48 is free to radially displace and disengage from the base 12 once the user continues to displace the needle hub 22 relative to the needle shield 24. The engagement of the detent 36 with the recess 42 and the engagement of the locking tab 38 with the inner shield latch shields the introducer needle 20 and thereby reduces the possibility of an accidental needle stick. FIG. 10 illustrates a completely deployed needle shield 24. The latch beam 48 is removed from the base 12 as the user continues to pull on the needle shield 24.

In another alternative embodiment, the needle hub assembly 10 can also be attached to a fluid connector and the base 12. This embodiment allows a user to prime the infusion device while it is outside the body and insert and remove the introducer needle 20 with the fluid connector attached the entire time.

Figure 11:
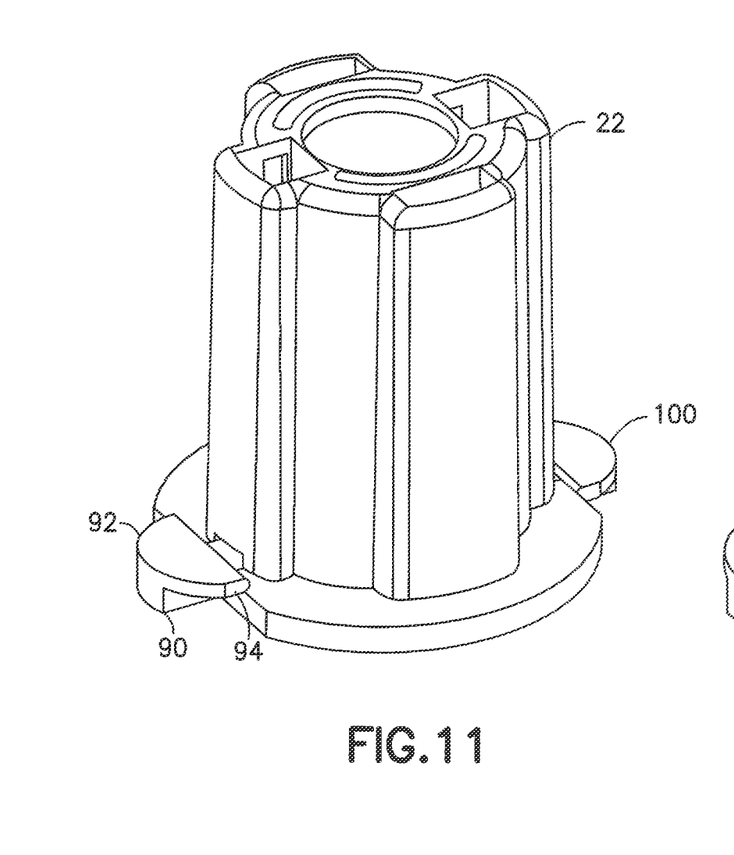
FIG. 11 is a perspective view showing another embodiment of the legs of the needle shield.
Figure 12:
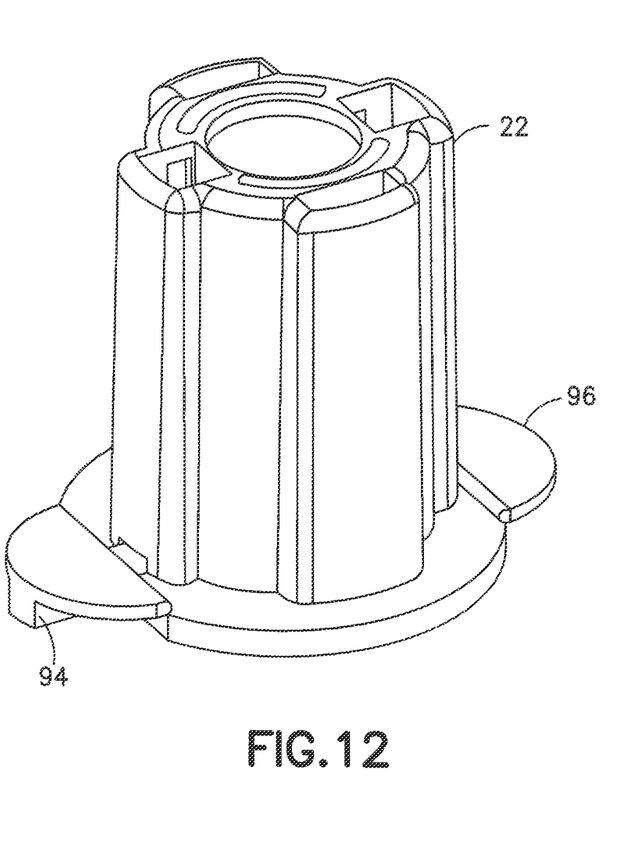
FIG. 12 is a perspective view showing the legs of the needle shield in a further embodiment.

In another embodiment shown in FIG. 11 the legs 70 forming the latch member of the needle shield 24 can include a latching tab 90 having a dimension greater than the latching tabs 74 of the pervious embodiment to provide increased surface area for the user to actuate the locking tabs 90 and release the flange of the needle hub 22. In the embodiments shown, the latching tabs 90 can have a curved outer edge 92 with blunt side edges 94. In the embodiment of FIG. 12, the latching tabs 96 have an increased surface area sufficient to enable the user to easily depress the locking tabs 96 downward relative to the needle hub assembly 10. The latching tabs 96 can have a semicircular shape as shown in FIG. 12.

Figure 13:
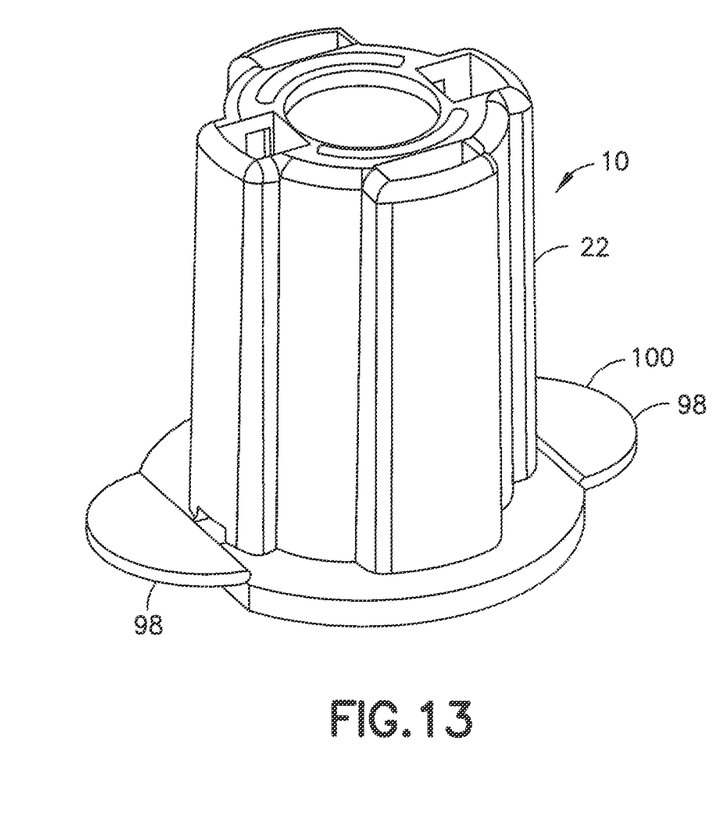
FIG. 13 is a perspective view showing the needle shield in another embodiment of the invention.
Figure 14:
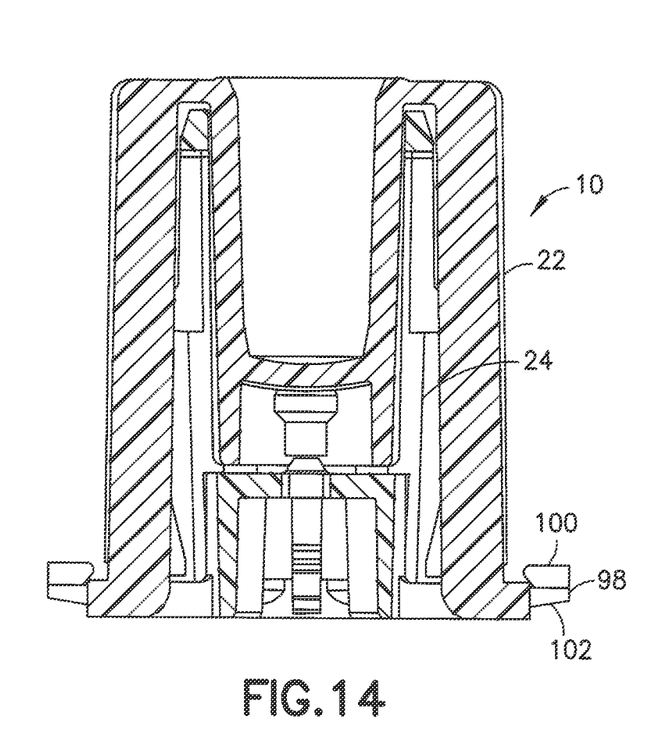
FIG. 14 is a cross-sectional side view of the needle hub and needle shield of FIG. 13 showing the undercut of the legs.

In another embodiment shown in FIGS. 13 and 14, the latching member includes flexible legs 98 and latching tabs 100. The legs 98 of the latching mechanism are formed with an undercut 102 to allow flexing of the legs in a downward direction toward the base to disengage the latching tabs 100 with the flange of the needle hub 22. In the embodiment shown the undercut 102 is in the form of an inclined surface relative to the longitudinal dimension of the legs shown in FIG. 14 to form a gap between the legs 98 and the base 12 where the legs 98 can flex downward to release the flange of the needle hub 22.

Figure 15:
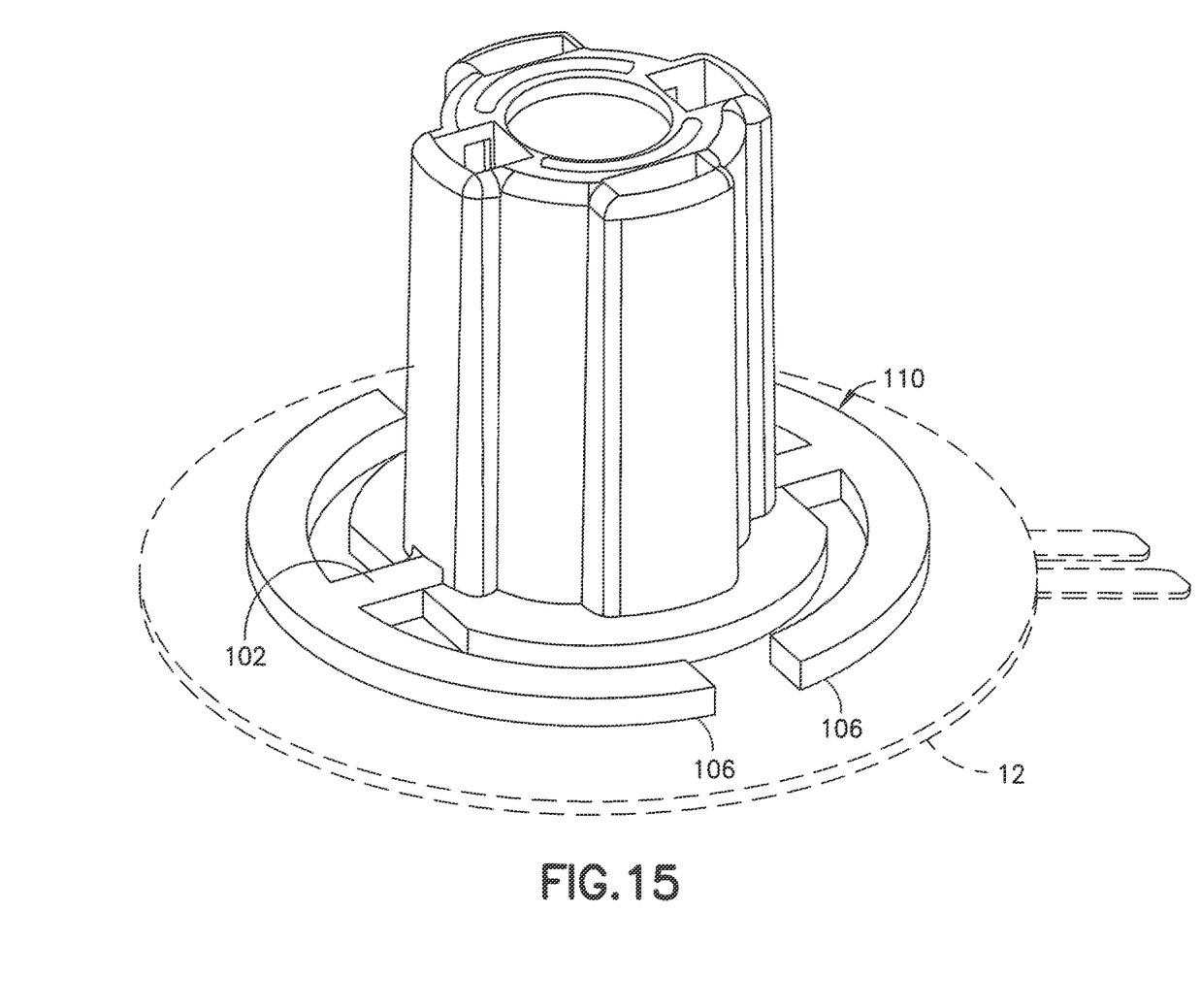
FIG. 15 is a perspective view of the needle hub and needle shield an another embodiment of the invention.
Figure 16:
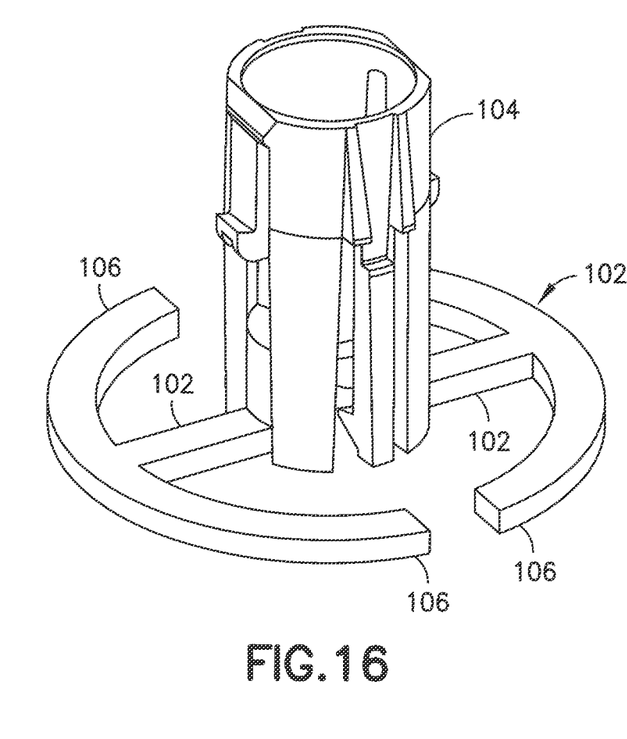
FIG. 16 is a perspective view of the needle shield of FIG. 15.
Figure 17:
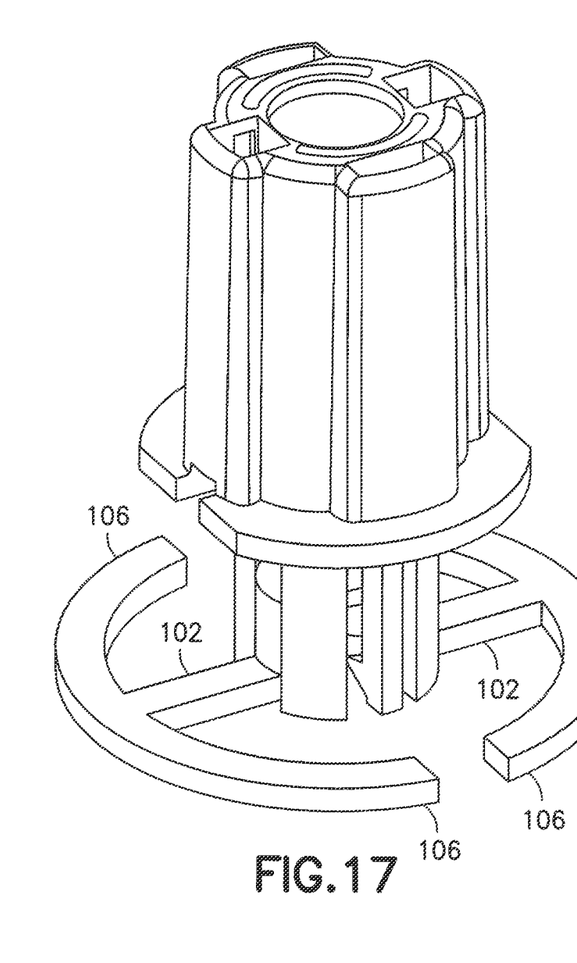
FIG. 17 is a perspective view of the needle shield in the extended position relative to the needle hub.

In another embodiment shown in FIGS. 15-17, the needle shield can include stabilizing members 110 extending from at least one side and typically two opposite sides as shown. The stabilizing members 110 have a dimension to contact the top surface of the base of the infusion device as depicted in FIG. 15 to stabilize the needle hub assembly and resist tilting and twisting the needle hub 22 assembly relative the base 12.

The stabilizing members 100 in the embodiment shown have a leg 102 extending outwardly in a radial direction from the needle shield 104 as shown in FIG. 16 and FIG. 17. At least one and typically two arms 106 extend laterally from the leg 102 to provide sufficient surface contact with the base 12 to stabilize the needle hub assembly 10. In the embodiment shown, the arms 106 have an arcuate shape forming a semicircle concentric with the outer edge of the needle hub assembly 10. The arms 106 preferably have a suitable length and configuration to support the needle hub assembly in an upright position and resist tilting. In one embodiment, the arms can be joined as a single unitary member to encircle the needle hub assembly.

The legs 102 in the embodiment shown have a substantially flat top surface although the top surface can be rounded or angled as needed. In a further embodiment, the top surface of the legs can include a latching tab as in the embodiments of FIGS. 1-14 to engage and couple with the flange of the needle hub 22 where the latching tabs can be separated by bending or deflecting to release the flange as in the previous embodiments.

In each of the disclosed embodiments and in other alternative embodiments, the components of the infusion device can be made of injection-molded polypropylene, polyethylene, acrylonitrile butadiene styrene polymers, polyesters such as polyethylene terephthalate or similar materials, and/or bio-based resins such as polylactide, starch-filled polypropylene, or polyhydroxyalkanoates. The catheter can be a separate component or it can be injection-molded as part of the base assembly, either as a single part or as a coinjection-molded part using two resins. Soft shot components can be of ethylene vinyl acetate, thermoplastic urethanes, styrenic thermoplastic elastomers, cellulosic elastomers, copolyester elastomers, or similar materials.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

The invention claimed is:

1. An infusion device comprising;
a base having a catheter and a coupling for connecting to a delivery device;
a needle hub having an insertion needle coupled to said needle hub and extending into said catheter, said needle hub having a bottom end for contacting said base; and
a needle shield received in said needle hub for axial sliding with respect to said needle hub from a first retracted position to an extended position to cover said insertion needle, said needle shield having a bottom end removably coupled to said coupling of said base, and said needle shield having at least one leg extending radially outward from said bottom end of said needle shield and having a distal end spaced radially outward from said needle shield and from said needle hub a distance to stabilize said needle hub relative to said base, said leg having a latching tab oriented radially outward from said needle hub and coupled to an outer surface of said needle hub, said latching tab being separable from said needle hub whereby said needle hub slides axially from said base, and said needle shield slides to said second position and said needle shield separates from said base.

2. The infusion device according to claim 1, wherein said at least one leg of said needle shield comprises two legs extending radially outward from opposite sides of said needle shield.

3. The infusion device according to claim 2, wherein each of said legs has a length to extend outwardly from said needle hub to couple with an outer edge of said needle hub.

4. The infusion device according to claim 3, wherein said legs are flexible and deflect toward said base to separate said latching tabs from said needle hub.

5. The infusion device according to claim 4, wherein said legs and latching tab are configured for manually deflecting toward said base to separate said latching tabs from said needle hub and retain said needle shield on said base during movement to said extended position.

6. The infusion device according to claim 2, wherein each of said legs have a distal end with arms extending outward in opposite directions from said distal end of said legs a distance to stabilize said needle hub and needle shield relative to said base.

7. The infusion device according to claim 6, wherein each of said arms have a substantially curved, arcuate shape.

8. The infusion device according to claim 1, wherein said at least one leg is flexible for bending between a first position where said latching tab is coupled to an outwardly extending flange at a bottom end of said needle hub and a second position releasing said needle hub to enable said needle hub to slide axially with respect to said needle shield.

9. The infusion device according to claim 8, wherein said latching tab has a latching surface facing radially inward with respect to said needle shield for coupling with an outer edge of said needle hub, and said latching tab has an upper face configured for manually deflecting said latching tab away from said needle hub.

10. The infusion device according to claim 1, wherein said needle hub has an outer sleeve contacting an outer surface said needle shield, said outer sleeve having an inwardly extending detent cooperating with a recess in an outer surface of said needle shield to lock the needle shield in said second extended position.

11. An infusion device comprising:
a base having a catheter and a coupling for connecting to a delivery device;
a needle hub having an insertion needle with a proximal end coupled to said needle hub and a distal end extending through said catheter, said needle hub having a bottom end for contacting said base; and
a needle shield received in said needle hub for axial sliding with respect to said needle hub from a first retracted position to an extended position to cover said insertion needle, said needle shield having a bottom end removably coupled to said coupling of said base, and at least one flexible leg extending radially outward from said bottom end of said needle shield, said leg having a latching tab oriented radially outward from said needle hub with an inwardly extending latching edge coupled to an outer surface of said needle hub to resist axial sliding of said needle hub relative to said needle shield, and said latching tab configured for deflecting said at least one leg toward said base to separate said latching tab from said needle hub.

12. The infusion device according to claim 11, wherein said at least one leg of said needle shield comprises two legs extending radially outward from opposite sides of said needle shield, and each said leg having a length to extend outwardly from said needle hub to couple with an outer edge of said needle hub.

13. The infusion device according to claim 11, wherein each of said legs include arms extending outward in opposite directions from a distal end of said legs a distance to stabilize said needle hub and needle shield relative to said base.

14. The infusion device according to claim 11, wherein said legs are flexible and include an undercut for deflecting said legs toward the base a downward force applied to said legs.

15. A needle hub assembly for an infusion device comprising:

a needle hub having an insertion needle with a proximal end coupled to said needle hub and a distal end adapter for extending through a catheter of said infusion device, said needle hub having an open bottom end configured for contacting a base of the infusion device; and a needle shield received in said needle hub for axial sliding with respect said needle hub from a first retracted positon within said needle hub and a second extended position extending from said open bottom end of said needle hub, and a first flexible leg and a second flexible leg extending radially outward from said needle shield and coupled to a bottom edge of said needle hub, each leg having a coupling tab coupled to an outer surface of said hub and having a length to contact the base of the infusion device to stabilize said needle shield relative to the base of the infusion device, said legs configured for deflecting toward said base to separate said coupling tab of said legs from said needle hub.

16. The needle hub assembly according to claim 15, wherein
said coupling tab of said legs are coupled to a radially extending flange on an outer edge of said needle hub.

17. The needle hub assembly according to claim 15, wherein
each of said legs include an undercut to enable said legs to bend toward said base.

* * * * *